United States Patent
Roesky et al.

(10) Patent No.: US 7,645,716 B2
(45) Date of Patent: Jan. 12, 2010

(54) OXYGEN-BRIDGED BIMETALLIC COMPLEX, THE PRODUCTION THEREOF AND ITS UTILIZATION FOR POLYMERIZATION CATALYSIS

(75) Inventors: Herbert Roesky, Gottingen (DE); Guangcai Bai, Windsor (CA); Vojtech Janicik, Gottingen (DE); Sanjay Singh, Gottingen (DE)

(73) Assignee: Georg-August-Universitaet Goettingen, Gottingen (DE)

( * ) Notice: Subject to any disclaimer, the term of this patent is extended or adjusted under 35 U.S.C. 154(b) by 100 days.

(21) Appl. No.: 10/593,029

(22) PCT Filed: Mar. 15, 2005

(86) PCT No.: PCT/EP2005/002741

§ 371 (c)(1),
(2), (4) Date: May 22, 2008

(87) PCT Pub. No.: WO2005/090373

PCT Pub. Date: Sep. 29, 2005

(65) Prior Publication Data

US 2008/0261804 A1  Oct. 23, 2008

(30) Foreign Application Priority Data

Mar. 17, 2004 (EP) ................. 04006357
Nov. 19, 2004 (DE) ............. 10 2004 055 922

(51) Int. Cl.
C08F 4/642 (2006.01)
C08F 4/643 (2006.01)
C07F 17/00 (2006.01)
B01J 31/12 (2006.01)
B01J 31/14 (2006.01)

(52) U.S. Cl. .............. 502/154; 502/153; 502/102; 526/943

(58) Field of Classification Search ............ None
See application file for complete search history.

(56) References Cited

U.S. PATENT DOCUMENTS 6,150,544 A    11/2000  Seki et al. ............ 556/27
6,528,448 B1    3/2003  Jensen et al. .......... 502/132

OTHER PUBLICATIONS

Pandit et al. Reaction of Dishloro Bis-Cyclopentadenyl Titanium With Dialkoxy Bis Chelated Titanium Compounds, Journal of the Less-Common Metals, 64 (1979) pp. 163-166.
G. Bai et al. Monouclear Aluminum Hydroxide for the Design of Well-Defined Homogeneous Catalysts, American Chemical Society, 2005, 127, pp. 3449-3455.

(Continued)

*Primary Examiner*—Melvin C Mayes
*Assistant Examiner*—James Corno
(74) *Attorney, Agent, or Firm*—Whitham Curtis Christofferson & Cook, PC

(57) ABSTRACT

The novel binuclear, oxygen-bridged, bimetallic complexes of the general formula (I):

$$[(LM^1R^1)(Cp_2M^2R^2)](\mu\text{-}O) \qquad (I)$$

are suitable as polymerization catalysts for olefin polymerization. ($M^1$=Al, Ge, Zr or Ti; $M^2$=Zr, Ti or Hf; Cp=cyclopentadienyl; $R^1$, $R^2$=methyl, ethyl, i-propyl, t-butyl, halogen, phenyl, alkylphenyl, $SiMe_3$; L=a bidentate, doubly heteroatom-coordinated organic chemical ligand, which together with the metal $M^1$ forms a 5 or 6-membered ring.) They display very good catalytic activities, good operating lives, and require little cocatalyst.

15 Claims, 5 Drawing Sheets

OTHER PUBLICATIONS

Lindsell et al. Reactions of Alkaline Earth Metal or Al Slurries With Bis-Cyclopentadienyl Complexes of Some Early Transition Metals, Polyhedron, vol. 5, No. 7, pp. 1259-1265, (1986).

Wang et al. Reactions of L2Zr(NMe 2)2 With Me3Al and PhC≡CH: Synthesis and Structural Characterization of New Zirconium Carborane Complexes [L2=Me2Si(C9h6)(C2B10H10) and Me2C(C5H4)(C2B10H10), Journal of Organometallic Chemestry 683 (2003), pp. 39-43.

Mach et al. The Isomerization Catalyst (C5H5)2TiCl2-LiAlH4, Influence of the Nature of Unsaturated Hydrocarbons on the Catalyst Activity, Journal of Organomerallic Chemistry, 269(1984), pp. 39-52.

Kauffman Silylation Coupled With Desilylation as a Route to Newer Syntheses, Polyhedron vol. 13, No. 13, (1994) pp. 2049-2054.

Klesing et al. The Effect of Substituents on Dimer Formation and Cation-Anion Interaction in Silicon Bridged Bisindenyl Zirconocene Propylene Polymerization Catalysts, Journal of the Chemical Society Faraday Transactions, (May 1, 1999), No. 9, pp. 2373-2377.

Ar = 2,6-iPr₂C₆H₃

Ar = 2,6-$iPr_2C_6H_3$

Figure 5: plot of TOF values for catalyst 3 over the MAO:catalyst ratios for catalyst 3 and Cp2ZrMe2

Figure 6: plot of reaction rates over time for catalyst 3 and Cp2ZrMe2

Figure 7: plot of reaction rates over time for catalyst 3 (MAO:cat = 48) and Cp2ZrMe2 (MAO:cat = 176)

OXYGEN-BRIDGED BIMETALLIC COMPLEX, THE PRODUCTION THEREOF AND ITS UTILIZATION FOR POLYMERIZATION CATALYSIS

The invention relates generally to the field of transition metal complex catalysts and metallocene catalysts for olefin polymerization.

Transition metal catalysts of the Ziegler-Natta type or catalyst systems developed therefrom have for a long time been widely used industrially as catalysts for low-pressure olefin polymerization, in particular the stereoselective polymerization of α-olefins. Chiral metallocene catalysts play an important role.

Cocatalysts used are organoaluminum compounds such as trialkylaluminum, alkylhaloaluminum, e.g. $AlEtCl_2$ or $AlEt_2Cl$, or, very widely, alkylaluminoxanes, in particular methylaluminoxane (MAO). To be able to achieve optimal catalytic activity for the respective system, a large excess of MAO cocatalyst is required. Thus, it is known that the catalytic activity of zirconocene-MAO systems decreases drastically below an Al:Zr ratio of about 200-300:1. It would therefore be desirable to have a catalyst which can be combined with smaller amounts of cocatalyst.

Since the mechanism of olefin polymerization catalyzed by transition metals is, like the structure of MAO, very complex and therefore not completely elucidated (Angew. Chem. 1995, 107, 1255-1283: "Stereospezifische Olefinpolymerisation mit chiralen Metallocencatalysatoren", H-H. Brintinger, D. Fischer, R. Mūlhapt, B. Rieger and R. Waymouth), the targeted design of such complexes is difficult. A wide variety of catalyst systems have been tried with varying success. The production of stereochemically very uniform polymers having a narrow molecular weight distribution and also a good operating life of the catalysts used are frequently desired.

It is an object of the invention to discover complexes having good catalytic activity in the polymerization of, in particular, olefins, which complexes avoid the disadvantages known in the prior art and have good operating lives and can be used particularly economically.

The invention achieves this object by providing suitable novel binuclear, oxygen-bridged, bimetallic complexes of the general formula (I):

$$[(LM^1R^1) Cp_2M^2R^2)](\mu\text{-O}) \qquad (I)$$

where:
$M^1$ = Al, Ge, Zr or Ti;
$M^2$ = Zr, Ti or Hf;
Cp = cyclopentadienyl;
$R^1$, $R^2$ = H; C(1-6)alkyl; halogen; aryl; $SiMe_3$ and alkyl-aryl where aryl = $C_6H_{5-n}X_n$ and X = halogen, C(1-6)alkyl, aryl, $NO_2$, $SO_3H$, $NR^3_2$, where $R^3$ = C(1-6)alkyl or H and n = 0 to 5; and L is a bidentate, doubly heteroatom-coordinated organochemical ligand which together with the metal $M^1$ forms a 5- or 6-membered ring. The heteroatom is preferably a nitrogen atom.

$M^1$ is preferably a main group metal, more preferably Al or Ge.

Possible halogens or halides are first and foremost chlorine, fluorine and bromine. As alkylphenyls, it is possible to use, in particular, monotrialkylphenyls, dialkylphenyls or trialkylphenyls. C(1-6)alkyl is any branched or unbranched alkyl radical having from 1 to 6 carbon atoms, preferably methyl, ethyl, i-propyl, n-propyl or t-butyl. Aryl is a benzene radical bearing from 1 to 6 substituents and encompasses phenyl. The aryl substituents can preferably be selected from the group consisting of halogen, C(1-6)alkyl, aryl, $NO_2$, $SO_3H$, $NR^3_2$, where $R^3$ = C(1-6)alkyl or H. In addition to phenyl, another preferred radical is mesityl.

It has surprisingly been found that the novel complexes are excellent polymerization catalysts, as will be demonstrated below with the aid of practical experimental data.

Preferred examples of the complexes of the invention are heterobimetallic complexes, in particular oxygen-bridged aluminum-zirconocene complexes, preferably complexes of the general formula $[(LAlMe) [Cp_2ZrR^2)] (\mu\text{-O})$, where $R^2$ is Me or Cl.

The ligand L preferably has the following composition of the formula II

(II)

corresponding to the structural formula:

where: X = C or P;
$R^a$ and $R^b$ can be the same radicals as indicated for $R^1$ and $R^2$, preferably H, methyl, ethyl, i-propyl, t-butyl,
phenyl, alkylphenyl; trimethylsilyl;
n = 1 when X = C; n = 2 when X = P.

The ligand more preferably has the composition $Ar\text{—}N\text{=}C(CH_3)\text{—}HC\text{=}C(CH_3)\text{—}N\text{—}Ar$, where $Ar = 2,6\text{-}iPr_2C_6H_3$ corresponding to the structural formula:

where Ar is an aromatic system and is in particular $2,6\text{-}iPr_2C_6H_3$.

To prepare the oxygen-bridged bimetallic complexes of the invention, we have found a process which is characterized in that a precursor complex of the formula $LM^1R^1$ (OH) is reacted with a metallocene precursor complex $Cp_2M^2(R^2)_2$ or $Cp_2M^2MeR^2$ or $Cp_2M^2HX$, where X = halogen, preferably in an inert solvent. Possible halogens are first and foremost fluorine, chlorine or bromine. Examples of the processes of the invention for preparing the complexes are given in the experimental part. These processes are also suitable for preparing heterobimetallic complexes in a targeted manner.

The invention also encompasses the use of binuclear, oxygen-bridged bimetallic, in particular heterobimetallic, complexes which have been formed from a transition metallocene and an organic Al, Ge, Zr or Ti compound which does not contain a cyclopentadienyl group, in particular a complex as claimed in any of claims 1 to 4, as polymerization catalysts. The complexes are particularly suitable for the homopolymerization or copolymerization of olefins, including α-olefins and cyclic olefins, for the cyclopolymerization of dienes and, if appropriate, for the polymerization of functionalized olefins. These catalysts are preferably used for the polymerization of low-pressure polyethylene.

As cocatalyst, preference is given to using a cocatalyst of the [MeAlO]x type, in particular methyl-aluminoxane (MAO), or else trialkylaluminum or an alkylhaloaluminum compound.

The invention therefore also encompasses catalyst preparations for the polymerization of olefins, which preparations comprise at least a binuclear, oxygen-bridged, bimetallic complex according to the invention and at least one cocatalyst. Preference is given to using alkylaluminoxanes and in particular methyl-aluminoxane (MAO) as cocatalysts. Among the catalyst complexes according to the invention, preference is given to the heterobimetallic complexes.

As demonstrated by the experimental results, the catalyst complexes of the invention display very good catalytic activity. They reach a stable activity plateau within a short time and have good operating lives. It is surprising that the amount of cocatalyst (in the example MAO) required can be reduced by a multiple with the aid of the complexes of the invention, in the example polymerizations carried out by up to 90%, compared to the $Cp_2ZrMe_2$ employed as reference.

EXPERIMENTAL PART—EXAMPLES

The preparation of example compounds is described below. The catalytic activity of these in the polymerization of ethylene was then examined. Here, the amount of cocatalyst was varied within a wide range.

A description of how LAlMe(OH) (2) can be obtained from the precursor compound LAlMeCl (1) by two different reaction routes will be given first.

The precursor compound (1) itself was synthesized as follows from commercially available starting materials: Synthesis of LAlMe(Cl) (1): LLi-OEt$_2$ (2.49 g, 5.00 mmol) in toluene (30 ml) was added dropwise to MeAlCl$_2$ (5.00 ml, 1.0 M in hexane, 5.00 mmol) in toluene (15 ml) at −60° C. The mixture was warmed to room temperature and stirred for 12 hours. Volatile constituents were removed under reduced pressure and the crude product was dissolved in hexane (100 ml). The finished solution was concentrated to 50 ml and allowed to stand overnight at −32° C. in order to obtain colorless crystals. An additional amount of 1 could be recovered from the mother liquor. Yield: (2.05 g, 83%). Mp: 190° C., $^1$HMNR (500 MHz, $C_6D_6$): δ=7.15-7.05 (m, Ar), 4.98 (s, 1H, γ-CH), 3.76 (sept, $^3J_{HH}$=6.8 Hz, 2H, CHMe$_2$), 3.21 (sept, $^3J_{HH}$=6.8 Hz, 2H, CHMe$_2$), 1.52 (s, 6H, CMe), 1.46 (d, $^3J_{HH}$=6.8 Hz, 6H, CHMe$_2$), 1.28 (d, $^3J_{HH}$=6.8 Hz, 6H, CHMe$_2$), 1.19 (d, $^3J_{HH}$=6.8 Hz, 6H, CHMe$_2$), 1.02 (d, $^3J_{HH}$=6.8 Hz, 6H, CHMe$_2$), −0.65 (s, 3H, AlMe); EI-MS: m/e (%); 479 (100) [M$^+$-Me]; elemental analysis, calculated for $C_{30}H_{44}AlClN_2$ (494): C, 72.9, H 8.9, N, 5.6; found: C, 72.8, H 9.0, N, 5.6.

The LAlMe(OH) (2) is reacted with zirconocenes (bis(η-cyclopentadienyl) zirconium complexes) to form two different complexes, namely [(LAlMe)(Cp$_2$ZrMe)] (μ-O) (3) and [(LAlMe)(Cp$_2$ZrCl)] (μ-O) (4).

The associated reaction equations are shown in the figures.

GENERAL

All handling was carried out under an atmosphere of purified nitrogen using standard Schlenk techniques. The samples for the recording of spectra and for reactions were processed in a glove box. The solvent was dried, distilled under nitrogen and degassed by customary methods before use.

The $^1$H-NMR spectra were recorded on a Bruker AM 200 nuclear magnetic resonance spectrometer using SiMe$_4$ as external standard. The mass spectra were recorded on a Finnigan MAT 8230 mass spectrometer using the EI-MS method. The strongest peak of an isotope distribution is tabulated. The IR spectra were recorded in Nujol between KBr plates on a Bio-Rad FTS-7 spectrometer. The elemental analyses were carried out at the analytical laboratory of the Institute for Inorganic Chemistry of the University of Göttingen.

Synthesis of the precursor complex LAlMe(OH) (2): 40 ml of ammonia were condensed onto a suspension of LAlMeCl (1, 1.98 g, 4.00 mmol), KOH (KOH >85%, H$_2$O 10-15%, 0.15 A, 2.33 mmol of KOH (85%), 1.28 mmol of H$_2$O (15%)) and KH (0.05 g, 1.25 mmol) in toluene (80 ml) at −78° C. while stirring. The mixture was stirred at this temperature for a further one hour. The excess ammonia was then allowed to evaporate from the reaction mixture over a period of 4 hours. During this time, the mixture was slowly warmed to room temperature. After filtration and subsequent concentration under reduced pressure (to 8 ml), the resulting colorless solution was kept at −20° C. for one week in order to isolate the colorless crystals of 2 (1.12 g). After separating off the crystals and subsequent partial removal of the solvent from the mother liquor, the colorless solution obtained was kept at −20° C. for two days, and an additional yield of 2 (0.19 g) was recovered. Total yield: 1.31 g (68%, measured on 1). M.p.: 192° C.; IR (Nujol) ṽ=3728, 1552, 1530, 1373, 1316, 1256, 1189, 1178, 1106, 1056, 1023, 940, 878, 805, 768, 757, 689, 614 cm$^{-1}$; $^1$H NMR (300 MHz, $C_6D_6$): δ=7.16-7.07 (m, Ar), 4.93 (s, 1H, γ-CH), 3.69 (sept, $^3J_{HH}$=6.8 Hz, 2H, CHMe$_2$), 3.25 (sept, $^3J_{HH}$=6.8 Hz, 2H, CHMe$_2$), 1.57 (s, 6H, CMe), 1.32 (d, $^3J_{HH}$=6.8 Hz, 12H, CHMe$_2$), 1.21 (d, $^3J_{HH}$=6.8 Hz, 6H, CHMe$_2$), 1.07 (d, $^3J_{HH}$=6.8 Hz, 6H, CHMe$_2$), 0.53 (s, 1H, OH); −0.88 (s, 3H, AlMe); EI-MS. m/e (%); 461 (100) [M$^+$ −Me]; elemental analysis: calculated for $C_{30}H_{45}AlN_2O$ (476.7): C, 75.6, H, 9.5, N, 5.9; found: C, 75.4, H 9.5, N 6.0.

Alternative synthesis of 2 from 1: 1,3-Di-tert-butyl-imidazol-2-ylidene (1.08 g, 6.00 mmol) in toluene (50 ml) were added to LAlMeCl (2.97 g, 6.00 mmol) in toluene (80 ml). The solution was stirred at room temperature for 10 minutes. Degassed and distilled water (108 μ, 6.00 mmol) was slowly added over a period of 30 minutes while stirring. The mixture was stirred for a further one hour. Volatile components were removed under reduced pressure and the crude product was extracted in hexane (150 ml), with the 1,3-di-tert-butylimidazolium chloride being filtered off through Celite. The solution finally obtained was concentrated (60 ml) and stored at −20° C. for two days in order to give colorless crystals. Yield: 2.45 g (86%).

Synthesis of [(LAlMe) (Cp$_2$ZrMe)] (μ-O) (3): Toluene (60 ml) was added to a mixture of 2 (0.48 g, 1.00 mmol) and Cp$_2$ZrMe$_2$ (0.25 g, 1.00 mmol). The mixture was stirred at room temperature for 2 hours and then at 100° C. for 24 hours. The resulting colorless solution was kept at room temperature for 48 hours in order to isolate colorless crystals of 3 (0.51 g) After concentrating the filtrate to 8 ml, the solution was kept at 0° C. for three days. A further 0.15 g of 3 was obtained. Yield: 0.66 g (93%.). M.p.: 385° C. (dec); IR (Nujol) $\tilde{v}$=1518, 1467, 1380, 1316, 1257, 1178, 1101, 1017, 936, 884, 798, 768, 643, 617, 449 cm$^{-1}$; $^1$H NMR (300 MHz, CDCl$_3$): δ=7.25-7.24 (m, Ar), 5.31 (s, 10H, Cp), 5.06 (s, 1H, γ-CH), 3.17 (sept, $^3J_{HH}$=6.8 Hz, 2H, CHMe$_2$), 3.15 (sept, $^3J_{HH}$=6.8 Hz, 2H, CHMe$_2$), 1.75 (s, 6H, CMe), 1.37 (d, $^3J_{HH}$=6.8 Hz, 6H, CHMe$_2$), 1.35 (d, $^3J_{HH}$=6.8 Hz, 6H, CHMe$_2$), 1.22 (d, $^3J_{HH}$=6.8 Hz, 6H, CHMe$_2$), 1.03 (d, J$_{HH}$=6.8 Hz, 6H, CHMe$_2$), −0.32 (s, 3H, ZrMe), −0.72 (s, 3H, AlMe); EI-MS: m/e (%): 695 (100) [M$^+$ −Me]; elemental analysis: calculated for C$_{41}$H$_{57}$AlN$_2$OZr (712.1): C, 69.2, H 8.1, N, 3.9; found: C, 69.3, H, 7.9, N, 3.9.

Synthesis of [(LAlMe) (Cp$_2$ZrCl)] (μ-O) (4) In a procedure similar to that used for the preparation of 3, toluene (60 ml) was added to a mixture of 2 (0.48 g, 1.00 mmol) and Cp$_2$ZrHCl (0.25 g, 1.00 mmol). The colorless solution obtained was kept at room temperature for 48 hours in order to isolate colorless crystals of 4(0.37 g). After concentrating the filtrate to 10 ml, the solution was kept at 0° C. for three days. A further 0.28 g of 4 was obtained. Yield: 0.65 g (89%). M.p.: 396° C. (dec); IR (Nujol) $\tilde{v}$=1530, 1466, 1380, 1315, 1254, 1181, 1098, 1022, 943, 860, 797, 778, 759, 725, 657, 617 cm$^{-1}$; $^1$H NMR (300 MHz, CDCl$_3$): δ=7.29-7.21 (m, Ar), 5.54 (a, 10H, Cp), 5.09 (s, 1H, γ-CH), 3.16 (sept, $^3J_{HH}$=6.8 Hz, 2H, CHMe$_2$), 3.15 (sept, $^3J_{HH}$=6.8 Hz, 2H, CHMe$_2$), 1.78 (s, 6H, CMe), 1.42 (d, $^3J_{HH}$=6.8 Hz, 6H, CHMe$_2$), 1.36 (d, $^3J_{HH}$=6.8, 6H, CHMe2), 1.24 (d, $^3J_{HH}$=6.8 Hz, 6H, CHMe$_2$), 1.02 (d, 3J$_{HH}$=6.8 Hz, 6H, CHMe$_2$), x0.66 (s, 3H, AlMe); EI-MS: m/e (%): 715 (100) [M$^+$−Me]; elemental analysis: calculated for C$_{40}$H$_{54}$AlClN$_2$OZr (732.5): C, 65.6, H, 7.4, N, 3.8; found: C, 65.5, H, 7.3, N, 3.9.

Polymerization of Ethylene

Catalyst (0.005 M in toluene, 4 ml, 20 μmol) was added to toluene (100 ml) in a 250 ml Schlenk flask. This solution was degassed and the system was then connected to an ethylene atmosphere (1013 mbar pressure). The associated aluminoxane (toluene solution) was added. After the mixture obtained had been stirred for an appropriate time, the reaction was stopped by means of ethanol and the white polyethylene (PE) was collected and dried. The results are shown in Table 1 and FIG. 5.

Determination of the TOF and the Polymerization Rate g gram of polyethylene were obtained in 0.5 hours. The TOF was then calculated according to:

$$TOF = \frac{g \text{ of PE}}{20 \times 10^{-6}(\text{mmol of } cat) \times 0.5(b)}$$

$$= \frac{g}{10} \times 10^6 (g \text{ of PE/mol } cat \text{ } h)$$

When the ethylene volume V (consumed when the pressure of the system has dropped to 27 mbar below atmospheric pressure) has been polymerized in t seconds (when t is less than 1 sec, it is difficult to determine the reaction time precisely), the reaction rate is r=V/t (Table 2 and FIG. 6).

Influence of the Concentration of 3 on the TOF

Explanations of the data in Table 1: using the method as described above, 3 (0.005 M in toluene, 3 ml, 15 μmol), for example, was added to toluene (100 ml). MAO (0.15 ml) was added while stirring. After 20 minutes, MAO (1.5 ml) was added and the polymerization was started. After the resulting mixture had been stirred for 30 minutes, PE (9.9 g) was obtained (Experiment No. A08). Using the same method, MAO (0.1 ml) was added to a solution of 3 (2 ml, 10 μmol). After 20 minutes, MAO (1.0 ml) was added again. After polymerization for 2 hours, PE (7.6 g) was obtained (Experiment No. A09). The results and conditions for various experiments are summarized in Table 1. The experiments denoted by A and B relate to the catalysts according to the invention, and the experiments denoted by D relate to reference experiments.

Influence of the Reaction time of 3 with MAO on the TOF

Using the same method, 1.7 ml or 3.4 ml of MAO were added to 3 (20 μmol). After 18 or 30 minutes, 6.2 g or 10.9 g, respectively, of PE were obtained (Experiment No. A 10 and A 11 in Table 1).

Figure 1:
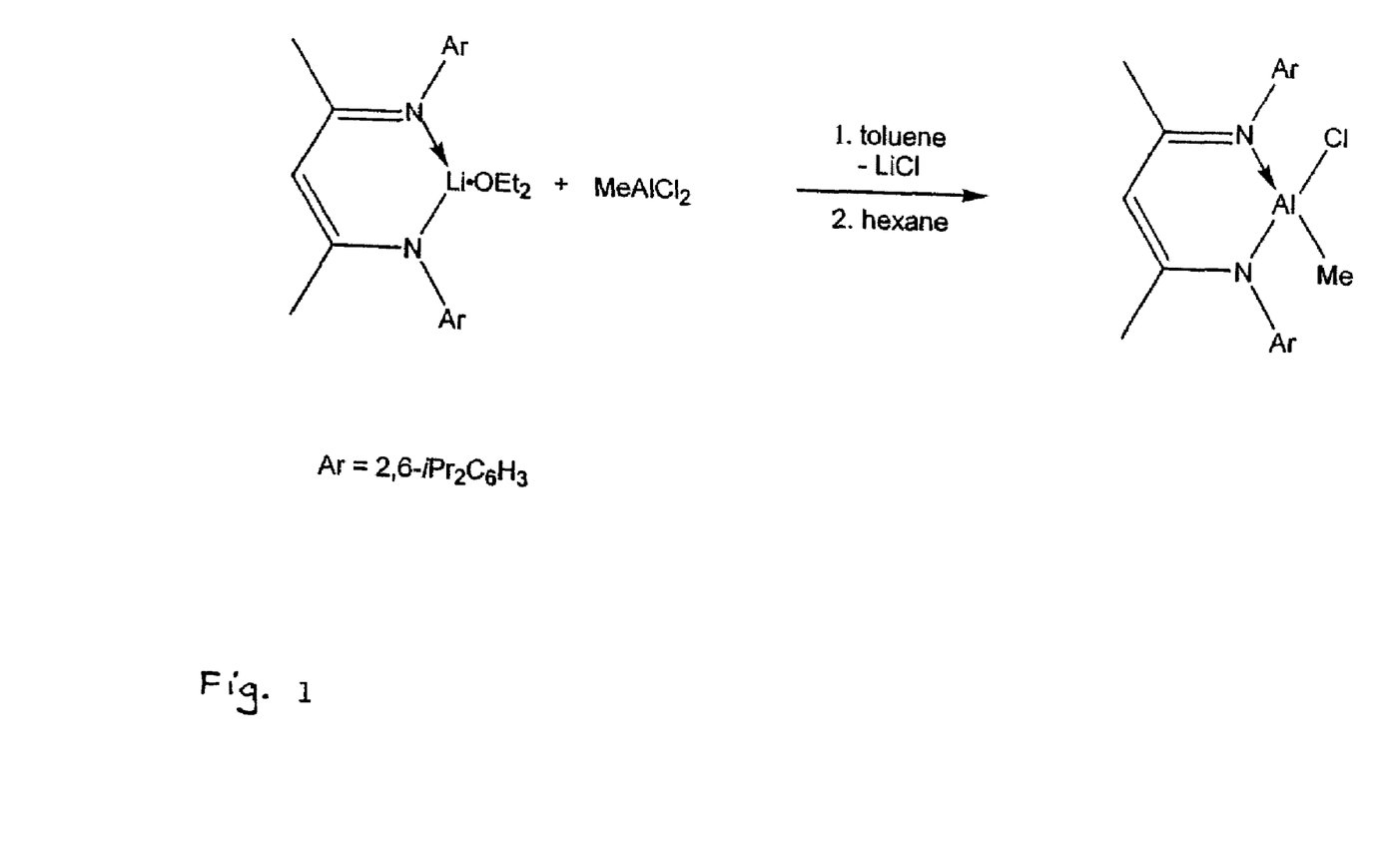
FIG. 1 shows the preparation of LAlMeCl from LLiOEt$_2$ and MeAlCl$_2$.
Figure 2A:
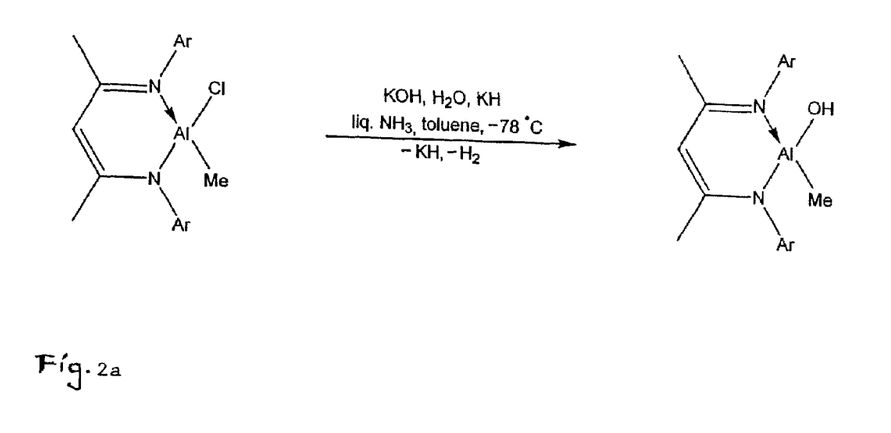
FIG. 2a shows the preparation of LAlMe(OH) from LAlMeCl using KH in a *strongly* basic medium.
Figure 2B:
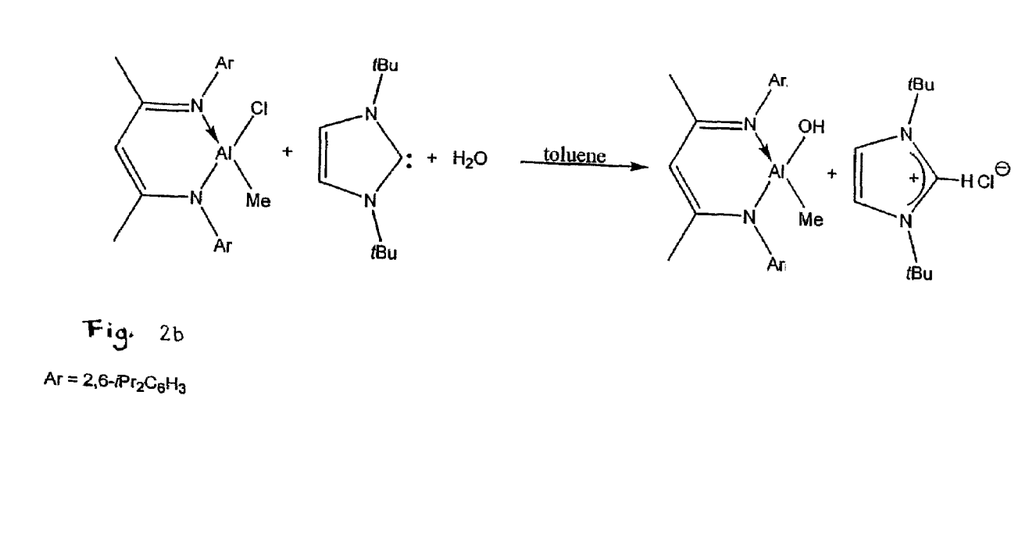
FIG. 2b shows the preparation of LAlMe(OH) from LAlMeCl using 1,3-di-t-butylimidazole.
Figure 3:
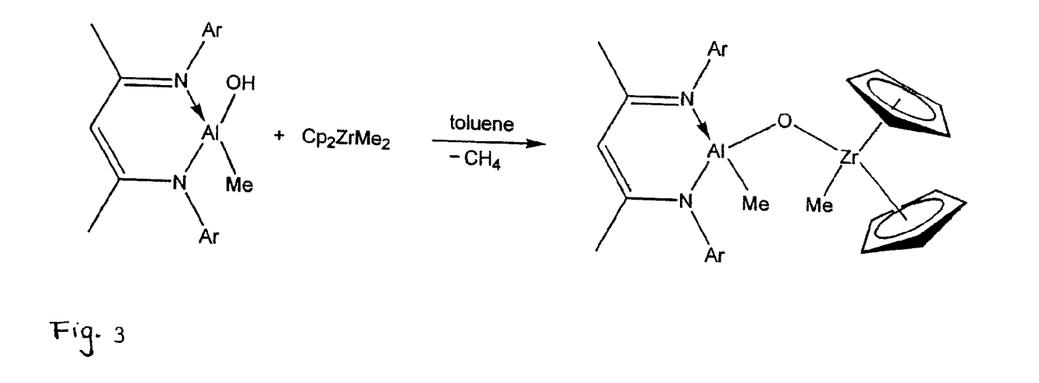
FIG. 3 shows the preparation of [(LAlMe) (Cp$_2$ZrMe)] (μ-O) from LAlMe (OH) and Cp$_2$ZrMe$_2$.
Figure 4:
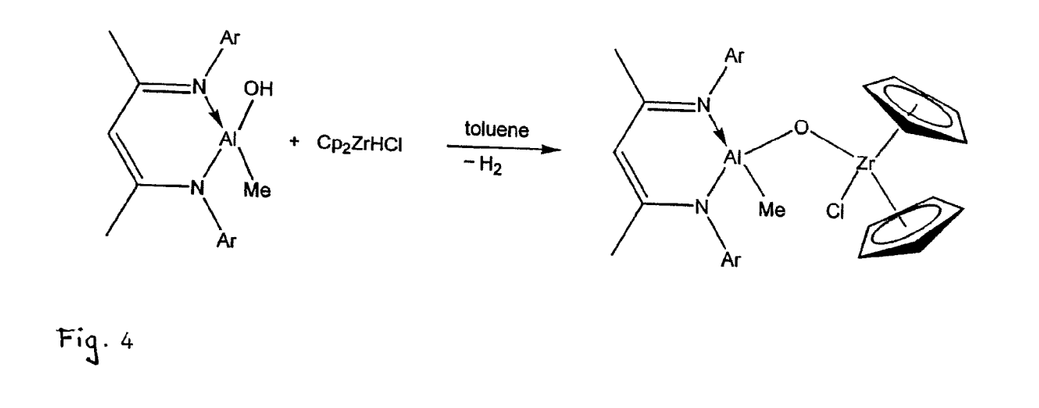
FIG. 4 shows the preparation of [(LAlMe) (Cp$_2$ZrCl)] (μ-O) from LAlMe (OH) and CP$_2$ZrHCl.
Figure 5:
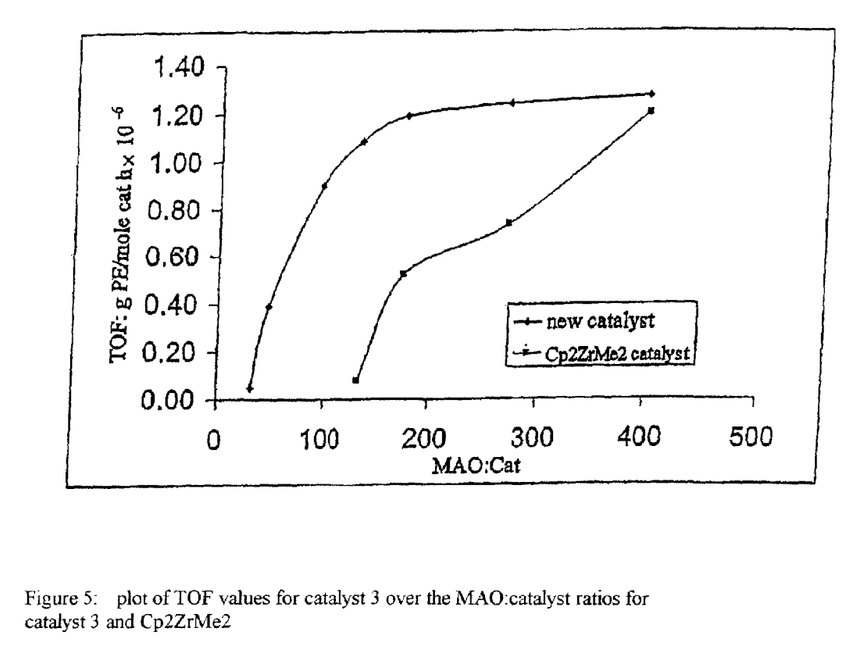
FIG. 5 shows a plot of TOF values for catalyst 3 compared to the reference catalyst.

The tabular data for 3 and the reference example are shown graphically in FIG. 5. It can be seen that the novel catalyst achieves a high value of the TOF even at very much smaller amounts of cocatalyst.

Figure 6:
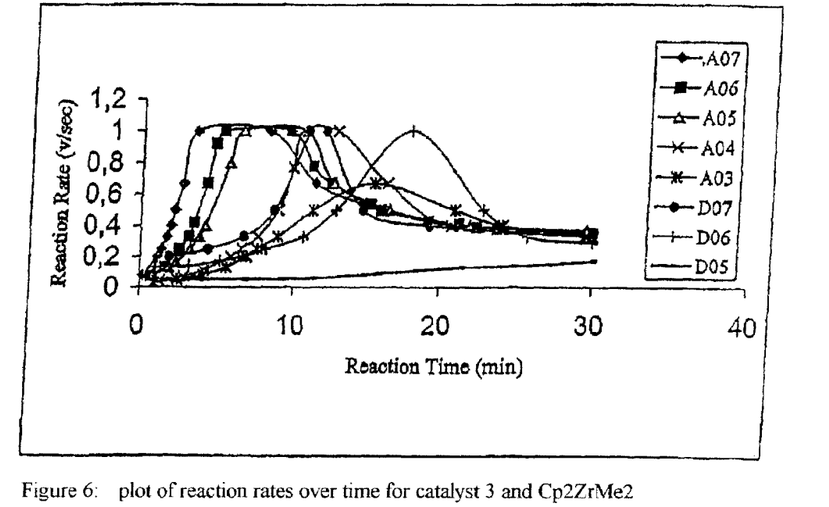
FIG. 6 shows a plot of reaction rates.

In FIG. 6, the reaction rate is plotted against the reaction time for 5 catalyst mixtures (A) with MAO and, for comparison, three Cp$_2$ZrMe$_2$ (D) systems with MAO. It can be seen that the novel catalyst mixtures (A07-A03) show constant behavior as a function of time, while this is not the case for the known (Cp$_2$ZrMe$_2$) mixtures.

Figure 7:
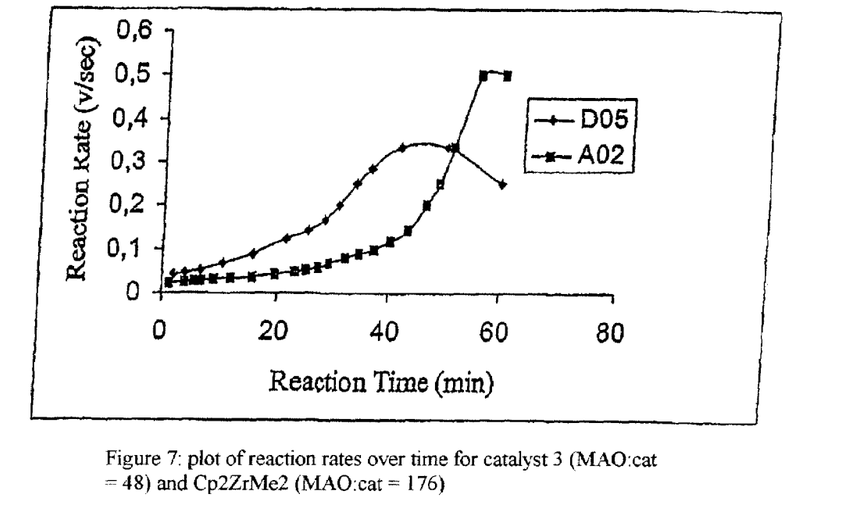
FIG. 7 shows the influence of the cocatalyst/catalyst ratio on the reaction rate.

In FIG. 7, the reaction rate is plotted as a function of the reaction time. Once for the novel catalyst system and MAO (A02) in a ratio of MAO to catalyst of 48:1 and, for comparison, Cp$_2$ZrMe$_2$ in a ratio of MAO to catalyst of 176:1 (DO5). It can clearly be seen that the novel system A02 still has about twice the reaction rate after 60 minutes. It has to be noted that only about a quarter of the amount of MAO was used in the novel A02 system.

TABLE 1

| | TOF (g of PE/mol · h × 10$^{-6}$) values for catalysts 3, 4 and Cp$_2$ZrMe$_2$ | | | |
|---|---|---|---|---|
| Catalyst* | MAO:cat | 1 (min) | PE (g) | TOF |
| 3 (A01) | 32 | 60 | 0.89 | 0.05 |
| 3 (A02) | 48 | 60 | 7.8 | 0.39 |
| 3 (A03) | 96 | 30 | 9.0 | 0.90 |
| 3 (A04) | 136 | 30 | 10.9 | 1.09 |
| 3 (A05) | 176 | 30 | 11.9 | 1.19 |
| 3 (A06) | 272 | 30 | 12.4 | 1.24 |
| 3 (A07) | 400 | 30 | 12.7 | 1.27 |
| 3 (A08) | 176 | 30 | 9.9 | 1.32 |
| 3 (A09) | 176 | 120 | 7.6 | 0.39 |
| 3 (A10) | 136 | 18 | 6.2 | 1.03 |
| 3 (A11) | 272 | 30 | 10.9 | 1.09 |
| 4 (B04) | 136 | 30 | 8.4 | 0.84 |
| 4 (B05) | 176 | 30 | 11.4 | 1.14 |
| Cp$_2$ZrMe$_2$ (D04) | 136 | 120 | 3.3 | 0.08 |
| Cp$_2$ZrMe$_2$ (D05) | 176 | 73 | 12.8 | 0.52 |
| Cp$_2$ZrMe$_2$ (D06) | 272 | 60 | 14.6 | 0.73 |
| Cp$_2$ZrMe$_2$ (D07) | 400 | 37 | 14.8 | 1.20 |

*For Experiments A01 to A07, 0.2 ml of MAO was added to a solution containing 3. After 20 minutes, the remaining MAO was added and the polymerization was started.

TABLE 2

Polymerization reaction rates r (V/sec.) for the catalysts 3 and Cp$_2$ZrMe$_2$

| A03 | | A04 | | A05 | | A06 | | A07 | | D05 | | D06 | | D07 | |
|---|---|---|---|---|---|---|---|---|---|---|---|---|---|---|---|
| t | r | t | r | t | r | t | r | t | r | t | r | t | r | t | r |
| 0.96 | 0.03 | 1.33 | 0.04 | 0.85 | 0.08 | 0.68 | 0.07 | 0.20 | 0.08 | 2.10 | 0.043 | 0.98 | 0.13 | 1.97 | 0.20 |
| 2.52 | 0.05 | 2.92 | 0.07 | 1.98 | 0.13 | 1.62 | 0.13 | 1.10 | 0.20 | 4.00 | 0.045 | 3.23 | 0.14 | 4.50 | 0.25 |
| 4.21 | 0.08 | 4.23 | 0.11 | 2.42 | 0.16 | 2.60 | 0.25 | 1.40 | 0.25 | 6.85 | 0.053 | 5.25 | 0.17 | 6.80 | 0.33 |
| 5.72 | 0.13 | 5.96 | 0.20 | 3.30 | 0.25 | 3.18 | 0.33 | 1.75 | 0.33 | 10.50 | 0.067 | 6.83 | 0.20 | 8.70 | 0.50 |
| 6.96 | 0.20 | 6.69 | 0.25 | 3.90 | 0.33 | 3.52 | 0.42 | 2.03 | 0.40 | 15.85 | 0.091 | 8.23 | 0.25 | 10.92 | 1.00 |
| 7.67 | 0.25 | 7.68 | 0.33 | 4.30 | 0.40 | 4.30 | 0.67 | 2.27 | 0.50 | 21.48 | 0.125 | 10.63 | 0.33 | 12.18 | 1.00 |
| 8.98 | 0.33 | 8.95 | 0.50 | 5.75 | 0.80 | 4.83 | 0.92 | 2.72 | 0.67 | 24.90 | 0.143 | 13.00 | 0.50 | 14.80 | 0.50 |
| 11.37 | 0.50 | 9.80 | 0.77 | 6.60 | 1.00 | 5.35 | 1.00 | 3.58 | 1.00 | 28.00 | 0.167 | 17.93 | 1.00 | 19.33 | 0.40 |
| 13.92 | 0.67 | 10.38 | 1.00 | 10.70 | 1.00 | 9.56 | 1.00 | 8.25 | 1.00 | 30.88 | 0.200 | 22.88 | 0.50 | 30.00 | 0.33 |
| 15.58 | 0.72 | 12.97 | 1.00 | 12.80 | 0.67 | 11.25 | 0.78 | 11.50 | 0.07 | | | 25.78 | 0.33 | | |
| 17.48 | 0.67 | 16.37 | 0.67 | 16.58 | 0.50 | 12.58 | 0.67 | 16.30 | 0.50 | | | 30.00 | 0.29 | | |
| 21.00 | 0.50 | 20.77 | 0.40 | 19.30 | 0.44 | 15.30 | 0.54 | 17.91 | 0.46 | | | | | | |
| 24.20 | 0.40 | 24.12 | 0.37 | 22.01 | 0.40 | 23.81 | 0.38 | 21.20 | 0.40 | | | | | | |
| 29.48 | 0.33 | 30.00 | 0.33 | 29.59 | 0.37 | 29.95 | 0.35 | 30.00 | 0.35 | | | | | | |

The invention claimed is:

1. A binuclear, oxygen-bridged, bimetallic complex of the general formula I:

$$[(LM^1R^1)(Cp_2M^2R^2)](\mu\text{-}O) \quad (I)$$

where:
M$^1$=Al, Ge, Zr or Ti;
M$^2$=Zr, Ti or Hf;
Cp=cyclopentadienyl;
R$^1$, R$^2$=H'; C(1-6)alkyl; halogen; aryl; SiMe$_3$; and alkylaryl where aryl =C$_6$H$_{5-n}$X$_n$
X=halogen, C(1-6)alkyl, aryl, NO$_2$, SO$_3$H, NR$^3{}_2$, where R$^3$=C(1-6)alkyl or H and n=0 to 5; and
L=a bidentate, doubly heteroatom-coordinated organochemical ligand which together with the metal M$^1$ forms a 5- or 6-membered ring.

2. The binuclear, oxygen-bridged, bimetallic complex as claimed in claim 1, in which
R$^1$, R$^2$=methyl, ethyl, i-propyl, t-butyl, halogen, phenyl, alkylphenyl, and SiMe$_3$, and
L is a bidentate, doubly nitrogen-coordinated organochemical ligand which, together with the metal M$^1$ forms the 5- or 6-membered ring.

3. The binuclear, oxygen-bridged, bimetallic complex as claimed in claim 1, wherein M$^1$=Al and M$^2$=Zr.

4. The binuclear, oxygen-bridged bimetallic complex as claimed in claim 3 wherein R$^2$ is Me or Cl.

5. The binuclear, oxygen-bridged, bimetallic complex as claimed in claim 1 wherein the ligand L is defined by formula II:

$$R^b\text{—}N\text{=}X(R^a)_n\text{—}HC\text{=}X'(R^a)_n\text{—}N\text{—}R^b \quad (II)$$

where X'=C or P; and
R$^a$, R$^b$=R$^1$, and n=1 when X=C, and n=2 when X=P.

6. The binuclear, oxygen-bridged, bimetallic complex as claimed in claim 1 wherein the ligand L is defined by formula III:

$$Ar\text{—}N\text{=}C(CH_3)\text{—}C(H)(CH_3)\text{—}N\text{—}Ar \quad (III)$$

where Ar is an aryl.

7. The binuclear, oxygen-bridged, bimetallic complex as claimed in claim 6 where in Ar is 2, 6-iPr$_2$C$_6$H$_3$ where iPr is isopropyl.

8. A process for preparing a binuclear, oxygen-bridged, bimetallic complex of the general formula I:

$$[(LM^1R^1)(Cp_2M^2R^2)](\mu\text{-}O) \quad (I)$$

where:
M$^1$=Al, Ge, Zr or Ti;
M$^2$=Zr, Ti or Hf;
Cp=cyclopentadienyl;
R$^1$, R$^2$=H'; C(1-6)alkyl; halogen; aryl; SiMe$_3$; and alkylaryl where aryl =C$_6$H$_{5-n}$X$_n$ X=halogen, C(1-6)alkyl, aryl, NO$_2$, SO$_3$H, NR$^3{}_2$, where R$^3$=C(1-6)alkyl or H and n=0 to 5; and
L=a bidentate, doubly heteroatom-coordinated organochemical ligand which together with the metal M$^1$ forms a 5- or 6-membered ring, comprising the step of reacting a precursor complex of the formula LM$^1$R$^1$(OH) with a metallocene precursor complex selected from Cp$_2$M$^2$(R$^2$)$_2$ or Cp$_2$M$^2$MeR$^2$ or Cp$_2$M$^2$HX" where X" is a halogen.

9. The method of claim 8 wherein said reacting step is performed in an inert solvent.

10. A catalyst preparation for the polymerization of olefins which comprises
at least one complex of the general formula I:

$$[(LM^1R^1)(Cp_2M^2R^2)](\mu\text{-}O) \quad (I)$$

where:
M$^1$=Al, Ge, Zr or Ti;
M$^2$=Zr, Ti or Hf;
Cp=cyclopentadienyl;
R$^1$, R$^2$=H'; C(1-6)alkyl; halogen; aryl; SiMe$_3$; and alkylaryl where aryl =C$_6$H$_{5-n}$X$_n$ X=halogen, C(1-6)alkyl, aryl, NO$_2$, SO$_3$H, NR$^3{}_2$, where R$^3$=C(1-6)alkyl or H and n=0 to 5; and
L=a bidentate, doubly heteroatom-coordinated organochemical ligand which together with the metal M$^1$ forms a 5- or 6-membered ring, and at least one cocatalyst.

11. The catalyst preparation as claimed in claim 10, wherein the at least one cocatalyst is an alkyl-aluminoxane.

12. The catalyst preparation of claim 11 wherein said alkyl-aluminoxane is methylaluminoxane.

13. A method of catalytically polymerizing polymers, comprising the steps of:
combining materials to be polymerized with a binuclear, oxygen-bridged, bimetallic complex of the general formula I:

$$[(LM^1R^1)(Cp_2M^2R^2)](\mu\text{-}O) \quad (I)$$

where:

$M^1$ = Al, Ge, Zr or Ti;
$M^2$ = Zr, Ti or Hf;
Cp = cyclopentadienyl;
$R^1$, $R^2$ = H'; C(1-6)alkyl; halogen; aryl; $SiMe_3$; and alkylaryl where aryl = $C_6H_{5-n}X_n$ X = halogen, C(1-6)alkyl, aryl, $NO_2$, $SO_3H$, $NR^3{}_2$, where $R^3$ = C(1-6)alkyl or H and n = 0 to 5; and
L = a bidentate, doubly heteroatom-coordinated organochemical ligand which together with the metal $M^1$ forms a 5- or 6-membered ring, and polymerizing the materials using said binuclear, oxygen-bridged, bimetallic complex as a catalyst.

14. The method of claim 13 wherein said combining step includes the step of adding an alkyl-aluminoxane, trialkyaluminum, or alkylhaloaluminum cocatalyst to said materials and said binuclear, oxygen-bridged, bimetallic complex.

15. the method of claim 14 wherein said cocatalyst is methylaluminoxane.

* * * * *